United States Patent
Zhang

(10) Patent No.: US 11,826,560 B2
(45) Date of Patent: Nov. 28, 2023

(54) RADIATION THERAPY TREATMENT PLANNING

(71) Applicant: RaySearch Laboratories AB, Stockholm (SE)

(72) Inventor: Tianfang Zhang, Stockholm (SE)

(73) Assignee: Raysearch Laboratories AB (Publ), Stockholm (SE)

( * ) Notice: Subject to any disclaimer, the term of this patent is extended or adjusted under 35 U.S.C. 154(b) by 0 days.

(21) Appl. No.: 17/999,708

(22) PCT Filed: May 19, 2021

(86) PCT No.: PCT/EP2021/063322
§ 371 (c)(1),
(2) Date: Nov. 23, 2022

(87) PCT Pub. No.: WO2021/244853
PCT Pub. Date: Dec. 9, 2021

(65) Prior Publication Data
US 2023/0191156 A1    Jun. 22, 2023

(30) Foreign Application Priority Data
Jun. 5, 2020  (EP) .................................. 20178508

(51) Int. Cl.
*A61N 5/10* (2006.01)
*G16H 20/40* (2018.01)

(52) U.S. Cl.
CPC .......... *A61N 5/1039* (2013.01); *A61N 5/1031* (2013.01); *A61N 5/1038* (2013.01); *G16H 20/40* (2018.01); *A61N 2005/1034* (2013.01)

(58) Field of Classification Search
CPC .. A61N 5/1039; A61N 5/1031; A61N 5/1038; A61N 2005/1034; G16H 20/40
See application file for complete search history.

(56) References Cited

U.S. PATENT DOCUMENTS

2005/0111621 A1    5/2005   Riker et al.
2007/0003011 A1*  1/2007   Lane .................... A61N 5/1031
                                                     378/65

(Continued)

OTHER PUBLICATIONS

McIntosh, C. et al (2017), Fully automated treatment planning for head and neck radiotherapy using a voxel-based dose prediction and dose mimicking method, Physics in Medicine & Biology, 62(15), 5926-5944.

(Continued)

*Primary Examiner* — Christine H Matthews
*Assistant Examiner* — Joshua Daryl D Lannu
(74) *Attorney, Agent, or Firm* — Noréns Patentbyrå AB

(57) ABSTRACT

A computer-implemented method for generating a radiation therapy treatment plan for a volume of a patient, the method comprising: receiving an image of the volume; receiving at least one dose-distribution-derived function configured to provide a value as an output based on, as input, at least part of a dose distribution defined relative to the image; receiving a first probability distribution and at least a second, different, probability distribution, the first and at least second probability distributions; defining a multi-criteria optimization problem comprising at least a first objective function based on the at least one dose-distribution-derived function, the first probability distribution and a loss function; and a second objective function based on the at least one dose-distribution-derived function, the second probability distribution and the loss function; and performing a multi-criteria optimization process based on the at least two objective functions to generate at least two output treatment plans.

15 Claims, 2 Drawing Sheets

(56) References Cited

U.S. PATENT DOCUMENTS

| | | |
|---|---|---|
| 2008/0226030 A1 | 9/2008 | Otto |
| 2009/0234626 A1 | 9/2009 | Yu et al. |
| 2010/0189220 A1* | 7/2010 | Flynn .................... A61N 5/103 |
| | | 378/65 |
| 2015/0367145 A1 | 12/2015 | Sjölund et al. |
| 2017/0014642 A1* | 1/2017 | An ....................... A61N 5/1031 |
| 2021/0020296 A1* | 1/2021 | Sjölund ................. G16H 50/20 |

OTHER PUBLICATIONS

International Search Report & Written Opinion, European Patent Office, dated Jul. 16, 2021, Rijswijk, Netherlands.
Office action dated Apr. 27, 2023 in corresponding Chinese patent application No. 202180039518.4, China.

* cited by examiner

RADIATION THERAPY TREATMENT PLANNING

TECHNICAL FIELD

This disclosure relates to an apparatus and method for radiation therapy treatment planning. In particular, the disclosure relates to an apparatus and method for radiation therapy treatment planning using a multi-criteria optimization process, and using probability distributions to represent knowledge obtained from historic treatment plans to derive a plurality of output treatment plans. The disclosure also relates to an associated computer program.

BACKGROUND

Radiation therapy treatment planning may be performed for different types of radiation therapy, such as external beam radiation therapy based on photons, light ions, or electrons, or brachytherapy.

In the field of radiation therapy treatment, a key challenge is to devise a high-quality treatment plan. A treatment plan may define an amount of radiation to be applied to a target volume for therapy and, for example, an amount of radiation that may be received by one or more organs at risk (OARs) or other bodily tissue during said therapy. There are processes that enable the creation of treatment plans and, in particular, the exploration and selection of those treatment plans to ensure the desired radiation dose is received by a target volume, such as a tumour, while causing as little damage as possible to healthy tissue and preferably no damage at all to OARs, such as the heart or the spinal cord.

One approach to the creation or improvement of a treatment plan comprises an optimization process that uses mathematical optimization techniques and, in particular, multi-criteria optimization (MCO). This MCO optimization process is usually based on an optimization problem comprising a plurality of objective functions and constraints. The objective functions may themselves be expressed as one or more functions. The objective functions used to form the multi-criteria optimization problem may be, to at least some extent, incompatible in the sense that improvement in the output from one objective function may require a deterioration in the output from one or more of the other objective functions. Each objective function that forms the MCO problem may be defined differently. Thus, an MCO process may yield a different treatment plan, e.g. first, second, third treatment plan etc., based on optimization of each of the objective functions. The MCO process thereby provides a plurality of candidate, output treatment plans from which a clinician may select a final treatment plan. In one or more examples it may be possible to interpolate (also known as to navigate) between the candidate, output treatment plans. MCO may be used to start from an idealized radiation dose distribution and to generate a plurality of candidate treatment plan options that each define a deliverable treatment plan.

The objective functions and constraints, and their respective component functions, used in the optimization problem may be considered quality measures for the treatment plan. An objective function may measure the deviation of a dose-measure from a desired value related to the dose distribution. It will be appreciated that in one or more examples the problem may include objective functions that are not evaluated based on an input dose distribution. The desired value of the dose-measure may be indicative of, for example, a minimum or maximum dose to a specific organ or volume. A constraint function may comprise a quality measure and/or define a set of feasible values the parameters of the treatment plan may take. Thus, in one or more examples, the feasible values may be configured to take account of the technical limitations of the radiation therapy delivery device. The quality measures should have mathematical properties that make them suitable for optimization, such as continuity and differentiability.

After an optimization problem has been defined, the most common way of arriving at a treatment plan is to find parameters representing said treatment plan that minimize or maximize each objective function while the constraints are satisfied.

The process of defining the optimization problem in an effective way to arrive at the candidate, output treatment plans is a challenge. There is thus a need for a process aimed specifically at effectively generating candidate treatment plans using MCO.

SUMMARY

According to a first aspect of the disclosure we provide a computer-implemented method for generating a radiation therapy treatment plan for a volume of a patient, the method comprising:
receiving at least one dose-distribution-derived function, the or each dose-distribution-derived function configured to provide a value as an output based on, as an input, at least part of a dose distribution defined relative to said image;
receiving a first probability distribution and at least a second, different, probability distribution, the first and at least second probability distributions representing the achievability or desirability of a range of the values output from said at least one dose-distribution-derived functions for an input dose distribution;
defining a multi-criteria optimization problem comprising at least two objective functions comprising:
a first objective function based on the at least one dose-distribution-derived function, the first probability distribution and a loss function; and
a second objective function based on the at least one dose-distribution-derived function, the second probability distribution and the loss function;
performing a multi-criteria optimization process based on said at least two objective functions to generate at least two output treatment plans.

In one or more examples, the step of performing a multi-criteria optimization process comprises performing at least two optimization procedures based on the multi-criteria optimization problem to generate a set of at least two output treatment plans. In one or more examples, the number of output treatment plans is at least the number of objective functions.

In one or more examples, the method includes determining a final treatment plan based on the at least two output treatment plans. The determination of the final treatment plan may be based on user input. In other examples, the determination may be automated and, in one or more examples, the method may include automated scoring of the at least two output treatment plans based on predefined criteria and the determination of the final treatment plan may be based on the output treatment plan that received the highest score.

In one or more examples, the method comprises receiving a plurality of dose-distribution-derived functions and the first probability distribution comprises a joint probability distribution for said plurality of dose-distribution-derived functions. In one or more examples, the method comprises receiving a plurality of dose-distribution-derived functions and the second probability distribution comprises a joint probability distribution for said plurality of dose-distribution-derived functions.

In one or more examples, the method comprises receiving a plurality of dose-distribution-derived functions and the first probability distribution comprises a plurality of marginal probability distributions for each of, or groups of, the plurality of dose-distribution-derived functions. In one or more examples, the method comprises receiving a plurality of dose-distribution-derived functions and the second probability distribution comprises a plurality of marginal probability distributions for each of, or groups of, the plurality of dose-distribution-derived functions.

In one or more examples, the method comprises modifying said first probability distribution to form the second probability distribution.

In one or more examples, said modification may be provided by application of a modification to a subset (e.g. one or more but not all) of the marginal probability distributions of the first or second probability distribution, such as those related to a corresponding subset of the dose-distribution-derived functions. In one or more examples, said modification may be provided by application of a modification to the only one or joint probability distribution, such as when the probability distribution collectively applies to the dose-distribution-derived functions.

In one or more examples, said modification of the first probability distribution to form the second probability distribution comprises one or more of:
 a change of a mean value of the first probability distribution;
 a change in a standard deviation of the first probability distribution;
 a change derived from exponential tilting of the first probability distribution; and
 a change of a skewness of the first probability distribution.

In one or more examples, the method includes modifying said first probability distribution to form a modified version thereof prior to said defining of the multi-criteria optimization problem and wherein the at least two objective functions comprise:
 the first objective function based on the at least one dose-distribution-derived function, the modified version of the first probability distribution and a loss function; and
 the second objective function based on the at least one dose-distribution-derived function, the second probability distribution and the loss function.

In one or more examples, said modification is determined based on one of:
 (i) user input defining said modification; and
 (ii) a plurality of default modifications; and
 the method includes providing feedback to an output device for a user, said feedback indicative of one or more of:
 (i) the different shapes of the first probability distribution and the second probability distribution due to said modification;
 (ii) the difference between characteristics of the first and second probability distributions due to said modification;
 (iii) an indication of how the dose-distribution for the volume will change due to said modification; and
 (iv) the output treatment plan determined as a result of said modification; and
 selecting said modification to apply based on user input that defines the modification, or user selection of one of the plurality of default modifications.

In one or more examples, said default modifications may be defined as a change in the mean or other characteristic by different numbers of standard deviations (e.g. one or two standard deviations) or by different predetermined percentages.

In one or more examples, the first probability distribution is determined from a database of previously delivered treatment plans, wherein the first probability distribution is representative of the likelihood of a range of the values of the at least one dose-distribution-derived function being achieved determined based on the dose distributions achieved in previously delivered treatment plans.

In one or more examples, said method comprises:
 receiving a current patient image comprising said image representing said volume of the patient to be treated and information identifying at least one bodily structure in said image;
 accessing a database having a plurality of records that represent dose distributions of previously delivered treatment plans and respective patient images with information identifying at least one bodily structure in said images;
 determining a measure of similarity between the current patient image and each of the patient images of said records, at least with respect to one or more of said at least one bodily structure;
 evaluating one or more of the dose-distribution-derived functions received for the current patient using the plurality of dose distributions of said records to obtain a dataset of values of the dose-distribution-derived function for each dose distribution;
 determining, from said dataset, said first probability distribution, corresponding to said evaluated one or more dose-distribution-derived functions, using a mapping function that gives a greater weighting to values of the dataset that correspond to a patient image having a greater measure of similarity with the current patient image and a lesser weighting to values of the dataset that correspond to a patient image having a lesser measure of similarity with the current patient image.

In one or more examples, the above method of deriving the probability distributions based on the measure of similarity between the current patient image and each of the patient images is applied for dose-distribution-derived functions that are configured to provide their respective values based on an input dose distribution represented as a dose-volume histogram. Thus, for such a dose-distribution-derived function, its output value only depends on the dose-volume histogram of the region of interest over which the function is defined. That is, its values for two dose distributions will coincide whenever the dose-volume histograms in the region of interest for said two dose distributions coincide.

In one or more examples, the second probability distribution is also generated using a database of records in a similar manner to the first probability distribution. The database may be a different database containing different records to that used for the first probability distribution. The different database may be a database of dose distributions that were achieved from treatment plans that may be categorised as being more aggressive by a clinician. Alternatively, it may be the same database, but a different subset of records may be used for generating the second probability distribution compared to the first probability distribution. In one or more examples, the records of the database may be categorised into a plurality of record sets and the first probability distribution may be generated from the one record set and the second probability distribution may be generated from a different record set. The difference between the record sets may be defined by a clinician or an automated process.

In a further example, the second probability distribution is also generated using a database of records in a similar manner to the first probability distribution. However, in one or more examples, a different mapping function is used to provide the different first and second probability distributions.

In one or more examples, if the dose-distribution-derived function is configured to provide its respective value based on predefined region of the volume and the input dose distribution is represented as a dose-volume histogram for said predefined region of the volume, the method comprises applying a weighting to said evaluated one or more dose-distribution-derived functions using the mapping function, wherein said mapping function comprising a monotone transformation of the measure of similarity; and if the dose-distribution-derived function comprises a single-voxel function, wherein said patient image is formed of a plurality of voxels and the dose-distribution-derived function is configured to provide an output equal to the dose delivered to a particular single voxel, the method comprises using a dose prediction model trained to predict the dose distribution of the current patient based on the patient image and information identifying at least one bodily structure in said image.

In one or more examples, the step of receiving the at least one dose-distribution-derived function may comprise receiving at least one function of each of said types.

In one or more examples, it will be appreciated that the method applied to the single-voxel type dose-distribution-derived function, may be equally applied to other non-dose-volume-histogram based dose-distribution-derived functions.

In one or more examples, the step of receiving the first probability distribution comprises:
  receiving a current patient image, x, comprising said image representing said volume of the patient to be treated and information identifying at least one bodily structure in said image; and
  based on the at least one dose-distribution-derived functions, $\{\psi_j\}_j$, each comprising a function of a dose distribution, d, over said patient image, estimating the conditional probability distribution:

$$p(\{\psi_j(d)\}_j | x, \{(x'', d'')\}_n)$$

using a machine learning process trained using training data comprising pairs $\{(x'', d'')\}_n$ of historic patient images $x''$ with information identifying said at least one bodily structure in said image and corresponding historic dose distributions $d''$ achieved in previously delivered treatment plans, the conditional probability distribution thereby being indicative of the likelihood of a range of outputs from the dose-distribution-derived functions for the dose distribution, d, for the current patient based on the dose distributions achieved for the historic patients.

In one or more examples, said first probability distribution comprises a Gaussian mixture model wherein parameters of said Gaussian mixture model are determined based on the at least one dose-distribution-derived function and dose distributions derived from the database of previously delivered treatment plans.

In one or more examples, the method comprises, based on user input, interpolating between the output treatment plans to define an interpolated treatment plan as the final treatment plan.

In one or more examples, the output treatment plans are defined in terms of one or more plan parameters and the method comprises, based on user input, interpolating said plan parameters between said output treatment plans to define an interpolated treatment plan as the final treatment plan.

In one or more examples, one or more of the at least one dose-distribution-derived functions is defined such that its input dose distribution is a dose distribution other than a dose-volume histogram (DVH). Thus, the dose-distribution-derived functions may be non-DVH-based.

In one or more examples, each of the output treatment plans comprises one of:
  a treatment plan defined in terms of operating parameters of a radiation therapy delivery device and from which a dose distribution over said volume can be derived;
  a treatment plan defined in terms of the dose distribution; and
  a treatment plan defined in terms of irradiation intensity integrated over time from each direction in space and from which a dose distribution over said volume can be derived.

In one or more examples, the step of receiving dose-distribution-derived functions comprises one or more of:
  receiving user input to define one or more of the dose-distribution-derived functions; and
  selection of one or more dose-distribution-derived functions from a set of candidate dose-distribution-derived functions, the candidate dose-distribution-derived functions comprising predetermined functions selected based on the part of the body of the patient in which said volume is defined.

In one or more examples, said dose-distribution-derived functions comprise, for the whole volume or part thereof, one or more of dose-at-volume, volume-at-dose, average dose, homogeneity comprising a measure of the dose homogeneity in the whole or part volume, conformity index, and a penalty function, including minimum-dose, maximum-dose or a dose-volume histogram function.

In one or more examples, the method comprises receiving the image of the volume and the dose distribution derived from the first and/or second treatment plan may be defined based on a plurality of voxels of said image. In one or more examples, the image comprises a plurality of voxels that define discrete sub-volumes of the image.

In one or more examples, the loss function is selected from one or more of:
  a logarithmic loss function; and
  a cross-entropy loss function.

In one or more examples, the method includes the step of: representing said one or more probability distributions, for each dose-distribution-derived function, as a cumulative distribution function or a probability density function in the optimization problem.

In one or more examples, the step of performing the optimization process includes:
  minimizing a selected objective function of the optimization problem to a point where the value of the other objective functions of the optimization problem deteriorates for any further change in the selected objective function; and selecting each of the other objective functions of the optimization problem as the selected objective function and repeating said minimizing.

In one or more examples, said step of receiving at least one dose-distribution-derived function comprises receiving at least two dose-distribution-derived functions.

Thus, in one or more examples, the present method may be advantageous in that the dose-distribution-derived functions may be converted to objective functions for forming at least part of the multi-criteria optimization problem by the process of forming a function of the dose-distribution-derived functions and one of the probability distributions and using it as input to the loss function.

According to a second aspect of the disclosure, we provide an apparatus for generating a radiation therapy treatment plan, the apparatus comprising a processor and a memory and computer program code stored in said memory, the computer program code configured to, when executed by said processor, cause the apparatus to perform the method of said first aspect. It will be appreciated that the optional features of the first aspect may be provided by said apparatus being configured to provide said functionality by said computer program code.

According to a third aspect of the disclosure, we provide computer program, preferably provided on a non-transitory computer readable medium, comprising computer program code that, when executed by a processor is configured to perform the method of the first aspect.

In one or more examples, the computer-implemented method of the first aspect is a method performed by a computing device. In one or more examples the method is performed by a computing device having an input device for receiving user input, a memory recall device for retrieving predetermined data from a database 106 or other memory and a processing device. In one or more examples, the steps of receiving the image of the volume and/or receiving the at least one dose-distribution-derived function and/or receiving the first and second probability distributions may be performed using the input device or the memory recall device. In one or more examples, the steps of defining the multi-criteria optimization problem and/or performing the multi-criteria optimization process and/or determining said final treatment plan may be performed by the processing device. In one or more examples, the computing device includes an output device which may output the determined output treatment plan or plans to a further apparatus, such as device 107 or to a user by way of an output device, which may comprise a visual display unit.

In one or more examples, the output treatment plan comprises data output from the apparatus which may be used to program a radiation therapy delivery device. In other examples, the output treatment plan may comprise data representing irradiation intensity integrated over time from each direction in space.

In one or more examples, the volume comprises or is represented by a three-dimensional image and the dose distribution derived from the output treatment plan or any treatment plan derived by the MCO process in arriving at the output treatment plan may be defined based on a plurality of discrete voxels of said image, said voxels defining discrete three-dimensional regions of the image.

In one or more examples, the apparatus includes an input device configured to receive an input drawn by a user representing a probability distribution.

According to a further aspect we provide an apparatus for generating a radiation therapy treatment plan, the apparatus comprising means for or at least one processing module configured to:

receive at least one dose-distribution-derived function, the or each dose-distribution-derived function configured to provide a value as an output based on, as an input, at least part of a dose distribution defined relative to said image;

receive a first probability distribution and at least a second, different, probability distribution, the first and at least second probability distributions representing the achievability or desirability of a range of the values output from said at least one dose-distribution-derived functions for an input dose distribution;

define a multi-criteria optimization problem comprising at least two objective functions comprising:
 a first objective function based on the at least one dose-distribution-derived function, the first probability distribution and a loss function; and
 a second objective function based on the at least one dose-distribution-derived function, the second probability distribution and the loss function;

perform a multi-criteria optimization process based on said at least two objective functions to generate at least two output treatment plans.

In one or more examples, a plurality of means or processing modules may be provided to each perform one or more of the respective actions: to receive the image of the volume, which may be electronically transferred thereto; to receive the at least one dose-distribution-derived function, such as by user specification or selection from predetermined candidates; to receive the first probability distribution, such as based on historical data records; to receive the second probability distribution, such as by duplicating the first probability distribution and making a modification thereto; to define the multi-criteria optimization problem; and to performing a multi-criteria optimization process. The optional features of the first aspect may also be performed by means or processing modules configured to perform the respective methods.

BRIEF DESCRIPTION OF THE DRAWINGS

There now follows, by way of example only, a detailed description of embodiments of the invention with reference to the following figures, in which.

DETAILED DESCRIPTION

Radiation therapy treatment planning is a complex task with many different factors playing a part. The size and position of a tumour within the body, the position and sensitivity of organs, so called organs at risk, around the tumour, the technical capabilities of the radiation therapy delivery device, and the clinical outcome of historical radiation therapy treatment may all contribute to the determination of a treatment plan.

Figure 1:
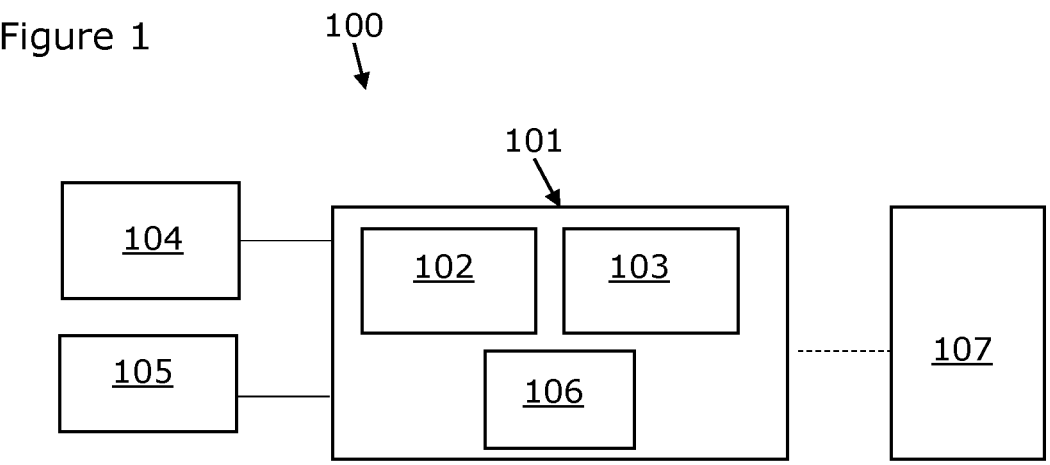
FIG. 1 shows an example apparatus for generating a radiation therapy treatment plan.

Example FIG. 1 shows an example treatment planning apparatus 100. The apparatus 100 may comprise a computer system 101 including a processor 102 and a memory 103 that is configured to perform a method defined by computer program code, which may be stored in said memory or otherwise provided to the computer system 101. It will be appreciated that the computer system 101 may comprise a terminal connected to a network, such as the Internet, and the processor and memory that perform the method may be located on one or more remote servers (not shown) with the terminal providing the interface to the user.

The treatment planning apparatus 100 may include an input device 104 to enable a user to enter information for performing treatment planning. In one or more examples, the input device 104 may enable preferences, selections of options presented, or other input to be entered, such as on a graphical user interface. In one or more examples, the input device 104 may enable the user to point to a displayed graphical item or draw an input pictorially. Accordingly, the input device 104 may comprise a stylus, mouse or touch screen interface among others. The treatment planning apparatus 100 may include a display device 105 coupled to the computer system 101 for display of information and/or presentation of the graphical user interface.

The treatment planning apparatus 100 may include access to a database 106 for receiving data records. In this example, for simplicity, the database 106 is shown as part of the system 101, although it will be appreciated that while it may be stored locally, it may alternatively be stored remotely from the computer system 101. Accordingly, the system 101 may include, in the alternative, a communication module 106 for obtaining information from the database, which may be stored on one or more data storage devices or servers accessible to said communication module.

In one or more examples, the treatment planning apparatus 100 may be coupled to or be capable of being coupled to a radiation therapy delivery device 107 for delivery of radiation to a patient. Accordingly, the treatment plan determined using the treatment planning apparatus 100 may be provided to the radiation therapy delivery device 107 for subsequent delivery thereby. In one or more examples, the treatment plan may be translated into operating parameters of the radiation therapy delivery device 107 or the treatment plan may already be defined in terms of operating parameters of the radiation therapy delivery device 107.

Multi-criteria optimization may be considered to be a type of treatment plan optimization in which a plurality of output treatment plans are generated based on a corresponding plurality of objective functions that form the optimization problem. It will be appreciated that in some examples, the number of treatment plans generated may be different to the number of objective functions, such as more than the number of objective functions. The objective functions may be considered to express the aims of the optimization processes on the same volume of the patient in different ways. A clinician may then make a judgement on which of the generated output treatment plans is preferred. In some examples, the treatment planning apparatus 100 may be configured to interpolate between the generated treatment plans allowing for the clinician to select a compromise between at least two different generated treatment plans.

It will be appreciated that the term "optimization" is used in the sense of gaining an improvement based on a defined measure rather than finding an absolute optimum solution. In general, an optimization of a treatment plan is a search for parameters of the treatment plan minimizing (or maximizing) as best as possible some objective function that evaluates the treatment plan subject to some constraints. For example, the parameters of the treatment plan may comprise operating parameters of the radiation therapy delivery device 107 (e.g. multi-leaf collimator positions, gantry rotation speeds over time, radiation beam power over time and any other operating parameter) and the objective function may be defined in terms of calculated radiation dose distribution delivered to a volume based on those operating parameters. The objective function may account for constraints, which may comprise technical limitations of the device 107. In other examples, the parameters of the treatment plan may be a fluence map, wherein the treatment plan parameters define the irradiation intensity integrated over time from each direction in space. Thus, it will be appreciated that the treatment plan may be defined in terms of many different types of parameters that define or are indicative of the radiation dose distribution over the volume of a patient to be treated. The dose distribution comprises a definition of how dose is distributed over a volume. The dose distribution may be defined in terms of the dose delivered to each of a plurality of voxels, the plurality of voxels comprising discrete volumes that form an image of the volume be treated. In general, the treatment plan may define the delivery of radiation and the dose distribution in the volume, in particular an electronic representation of the volume, may be derived therefrom.

In one or more examples, the starting point for the optimization process may comprise a treatment plan having parameters in which a guess, such as a qualified guess based on the experience of a clinician, of their appropriate values has been made (known in the art as a cold start). For example, a cold start treatment plan may be defined in terms of one or more of randomly chosen plan parameters; or plan parameters which correspond to delivering an average dose in the target volume (or a target approximate to the target volume) equal to an associated prescribed dose level. The optimization process described herein is indifferent to whether the treatment plan that comprises the starting point is realizable, in that it represents a treatment plan the device 107 is technically capable of delivering, or whether the treatment plan is idealized in that it may or may not be deliverable by the radiation therapy delivery device 107. Further the treatment plans generated by the present method may be represented in a variety of ways, such as in terms of the radiation therapy delivery device 107 operating parameters or as a dose distribution, which may be an idealised dose distribution. While, in some examples, the method described herein may begin with a treatment plan, in others it may not. Thus, alternatively, the treatment plan may be derived by the solving of the optimization problem, wherein the optimization problem is constructed using the desired plan parameters and is guided by the clinical goals defined in the optimization problem.

Accordingly, each objective function of the optimization problem defined later herein may be defined in terms of the operating parameters of the device 107 or as an irradiation intensity integrated over time from each direction in space (among other ways) and from which a dose distribution to a volume to be treated (which may be represented as a patient image of voxels) can be determined. The dose distribution can then be used as input to the dose-distribution-derived functions, which will be described later. As will be known to those skilled in the art, there are various methods, known generally as dose deposition mapping, that exist for translating plan parameters to a form suitable for assessing the dose delivered over the volume.

Thus, in summary, it will be appreciated that the starting point for the present method may comprise a first treatment plan, which may comprise a realistic treatment plan that is achievable given the constraints of the operating parameters of a radiation therapy delivery device, for example, or other constraints. In other examples, the first treatment plan may be an idealised treatment plan in that it may not have been determined whether it is achievable or not. In other examples, the method does not start with an idealized or realizable treatment plan and the plan parameters of the output treatment plans are defined in the formulation of the optimization problem.

Accordingly, the MCO optimization process described in the examples herein may be configured to derive a treatment plan by modifying an original objective function to obtain a plurality of objective functions that are derived from a plurality of dose-distribution-derived functions in different ways. The solving or partial solving of the MCO-type optimization problem leads to a plurality of output treatment plans, as will be described herein.

Figure 2:
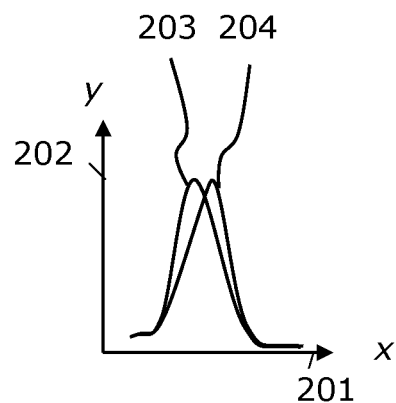
FIG. 2 shows example first and second probability distributions.
Figure 3:
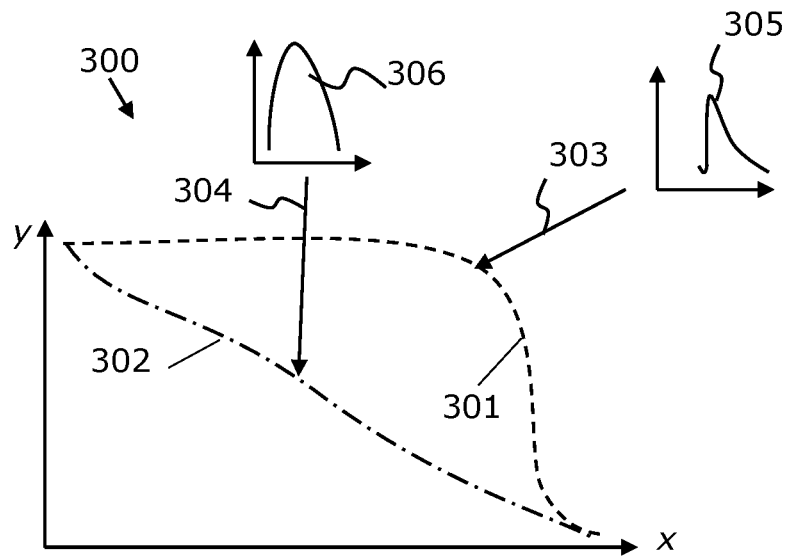
FIG. 3 shows the example dose-volume histogram for a part of the patient image and schematically shows the definition of a dose-distribution-derived function with an associated first probability distribution and a second probability distribution.
Figure 4:
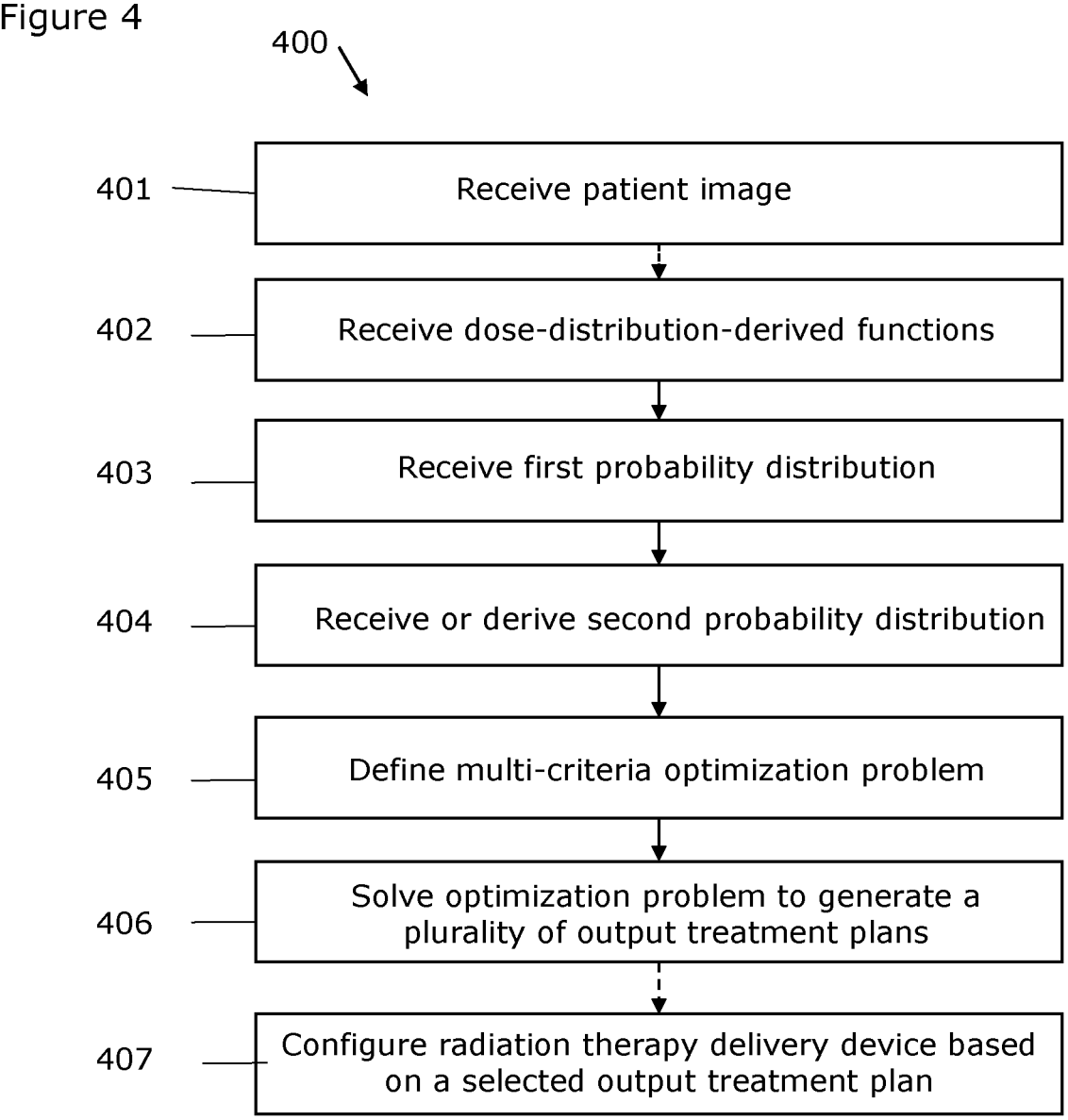
FIG. 4 shows a flow chart illustrating an example method for generating a radiation therapy treatment plan for a volume of a patient.

With reference to example FIGS. 2, 3 and 4 we will describe an example method 400 performed by said treatment planning apparatus 100.

The example method relates to multi-criteria optimization and the generation of a plurality of radiation therapy treatment plans, termed the output treatment plans in the examples that follow. The output treatment plans may be defined in terms of parameters that define how radiation should be delivered to a volume of a patient.

With reference to FIG. 4, example step 401 comprises receiving a patient image that represents a volume of the patient to be treated. In this example, the image comprises a three-dimensional image formed of a plurality of voxels that define discrete sub-volumes of the volume to be treated. The patient image may be associated with further information that identifies the bodily structures represented in the image, such as which voxels relate to a particular bodily structure. Thus, the voxels that represent organs at risk may be defined in the information as well as the voxels that represent the tumour. It will be appreciated that other structures and properties thereof may be designated in the information. As will be familiar to those skilled in the art, the image with the associated bodily structure information may be known as a contoured patient image.

The dose distribution derived from the treatment plans determined by the present example method may be defined based on the plurality of voxels of said image, wherein the dose delivered to each voxel, representing a sub-volume of the volume to be treated, may be calculated. Thus, each voxel or groups of voxels may be assigned a value representing the dose that voxel or group of voxels would receive based on the treatment plan being generated. The image typically comprises the output from a computed tomography (CT) scanner, such an x-ray or positron emission tomography-based scanner, or a magnetic resonance imaging (MRI) scanner, although other medical imaging techniques may be used.

While the method may use a patient image formed of voxels it will be appreciated that the volume of the patient that is the subject of the treatment planning method may be represented in any form, such as a data structure in the memory 103.

Step 402 comprises receiving one or more dose-distribution-derived functions. Such functions may be known in the art as dose statistics or clinical goals. The clinician/user (or an artificial intelligence, AI, agent) may specify or input the dose-distribution-derived functions to control the optimization process in a way that achieves effective treatment planning for the patient. The input may define one or more of regions of the volume, dose-related requirements or the functions themselves, as will be described below. Each dose-distribution-derived function comprises a function that provides a numeric value as an output based on, as an input, at least part of the dose distribution in terms of at least part of or all of the volume over which it is defined. Accordingly, the dose-distribution-derived function may take as input the dose distribution over a sub-volume of the total voxels (e.g. one or more of the voxels) or the dose distribution over the whole volume of voxels. The numerical value provided by a dose-distribution-derived function will be termed the dose-measure value for ease of reference.

According to examples of the disclosure, it may be desired to make adjustments to the parameters of a treatment plan in an optimization process involving values obtained from the dose-distribution-derived functions, wherein the dose distribution is derivable from the parameters of the treatment plan. The dose-measure can be used as a rating against a rating scale, wherein the rating scale may be represented by another function. It will be appreciated that a dose-distribution-derived function may be used as an objective function in an optimization problem. For example, taking a dose-distribution-derived function, m, that determines the mean dose of a distribution d, $m(d)=1/n\Sigma_{i=1}^{n}d_i$, it may be desired for the volume to have a mean dose of 6000 cGy. Therefore, an objective function, f, may be derived from the dose-distribution-derived function, as follows $f(d)=(m(d)-6000)^2$. It will be appreciated that both f(d) and m(d) receive a dose distribution as input, but f(d) is associated with a target and can be used in the MCO problem described later, wherein m(d) is not associated with a target and determines a dose-measure comprising, in this example, the mean dose. Thus, the dose-distribution-derived function may determine a dose-measure rather than a value representing a dose-measure relative to a target.

The dose-measure value output by the or each dose-distribution-derived function is to be used, in part, to drive the optimization. Thus, the dose-distribution-derived function is configured to output the dose-measure value which can be used to derive a rating. The rating may take a high value or a low value when the dose distribution provided to the associated dose-distribution-derived function is desirable relative to a target. The dose-distribution-derived functions may be determined by a user, such as a clinician, and/or may be selected from a set of candidate dose-distribution-derived functions.

Thus, in one or more examples, the step 402 of receiving the dose-distribution-derived functions comprises receiving user input, such as via input device 104, to define one or more of the dose-distribution-derived functions. The user input may comprise selection of a region in one or more images of the volume and associating with that selected region a dose-related requirement. The dose-distribution-derived function(s) may be determined based on this user input. Thus, in one or more examples, the user may define a sub-volume of the volume and enter a dose-related target, such as minimum dose, maximum dose or other target requirement, and the dose-distribution-derived function may be, at least in part, based on said user definition.

In one or more other examples, the step 402 comprises selection of one or more dose-distribution-derived functions from a set of candidate dose-distribution-derived functions.

In one or more examples, the candidate dose-distribution-derived functions are determined based on the part of the body of the patient in which said volume is located. Accordingly, predetermined dose-distribution-derived functions may be associated with different parts of the body and then selected as candidates by the system 101 based on the part of the body of interest, e.g. represented in the patient image. In one or more examples, the method may include the user identifying bodily organs in the volume or the computer system 201 identifying bodily organs in the volume, such as based on predetermined organ identification data, and presenting for selection a plurality of predetermined "candidate" dose-distribution-derived functions that are pre-associated with said identified organs.

The or each dose-distribution-derived function may be, for the whole volume or part thereof, a function that determines one or more of the dose-at-volume with respect to a predetermined part or all of the volume (such as in terms of a percentage of the volume), the volume-at-dose with respect to a predetermined dose level, or the average dose. The or each dose-distribution-derived function may be, for the whole volume or part thereof, a function that determines the homogeneity index with respect to a predetermined part or all of the volume (such as in terms of a percentage of the volume), representing the dose homogeneity in the target volume or sub-volume thereof. The or each dose-distribution-derived function may be, for the whole volume or part thereof, a function that determines the conformity index with respect to a predetermined isodose level. The conformity index of a treatment plan may be defined as a ratio between the volume covered by a reference isodose level and the target volume. It will be appreciated that there are a plurality of definitions of and algorithms for calculating homogeneity index and conformity index but for the purpose of this disclosure it does not matter which is used.

The or each dose-distribution-derived function may be, for the whole volume or part thereof, a penalty function, such as a quadratic-penalty function. Types of quadratic-penalty functions include minimum-dose functions, maximum-dose functions or dose-volume histogram functions.

A dose-distribution-derived function may be, for the whole volume or part thereof, a so-called single-voxel function with respect to some voxel, which outputs the dose delivered to said voxel. In one or more examples, the set of candidate dose-distribution-derived functions includes the corresponding single-voxel function for each of the voxels in the volume. Thus, in the above examples of the dose-distribution-derived functions, the reference to a part of the volume may comprise a single voxel in one or more examples. In other examples, the dose-distribution-derived function may be a so-called dose-volume histogram (DVH) based function wherein the dose-distribution-derived function is configured to provide its respective value based on a predefined region of the volume and the input dose distribution is represented as a dose-volume histogram for said predefined region of the volume.

In general, the dose-distribution-derived function may be any function taking as input the dose distribution and giving as output a single number for some region of interest of the volume (that is, a single voxel or a group of voxels). The number, i.e. the dose-measure value, comprises a dose-related statistic which may be compared to a dose-related target. The dose-distribution-derived function may be of single-voxel type in which they determine the dose delivered to a single voxel. The dose-distribution-derived functions may be of DVH type in which they are configured to act on a particular region of the volume to be treated and take as input a dose-volume histogram (i.e. data representative thereof) of said particular region.

Step 403 comprises receiving the dose-related target for the respective dose-measure value of the dose-distribution-derived functions in the form of a first probability distribution. Thus, the dose-measure value or values output by the dose-distribution-derived function or functions may be assigned a first target to move towards in the optimization process in the form of the first probability distribution. The first probability distribution is preferably determined based on historical data, as will be described below. However, as an alternative, a clinician may specify a target dose-measure that they wish to achieve by the optimization process in the form of a probability distribution. The probability distribution may be considered to represent a degree of preference or a degree of achievability for a range of the values output from said dose-distribution-derived functions for an input dose distribution. It will be appreciated that degree of preference may represent the preference of a clinician and therefore the degree of preference may also be understood as a degree of acceptance of the dose-measure value relative to the target. The first probability distribution may be a predetermined distribution based on the dose-distribution-derived functions selected at step 402.

The method may include receiving a plurality of dose-distribution-derived functions and the first probability distribution may comprise a joint probability distribution or a plurality of marginal probability distributions. A joint probability distribution collectively represents the targets for the optimization process for a plurality of the dose-distribution-derived functions. Alternatively, the first probability distribution may be represented as a plurality of marginal probability distributions for each of, or groups of, the plurality of dose-distribution-derived functions.

In the examples described herein, the first probability distribution is a joint probability distribution representing a range of targets collectively for the set (e.g. a plurality) of dose-distribution-derived functions. In such a case, the method may assume independence between the separate dose-distribution-derived functions and derive the probability distribution for the set. Alternatively, the method may use predetermined correlation data to derive the probability distribution for the set of dose-distribution-derived functions from the probability distributions for each of the constituent dose-distribution-derived functions, wherein the correlation data may be indicative of how different dose-distribution-derived functions may be interrelated to one another.

The use of a probability distribution rather than single target values for the dose-distribution-derived functions may provide the ability to better represent the goals and preferences of the clinician user when performing treatment planning and/or may provide for more effective and efficient optimization because the degrees of clinical relevance/satisfactoriness associated with different dose-measure outputs from the dose-distribution-derived functions may be more effectively characterised by a probability distribution. Thus, the use of a probability distribution instead of a single target value may be advantageous in that it can be seen as a "fuzzy" target value and may therefore provide more information for the optimization process than the use of a single target value, particularly when the first probability distribution is determined based on historical data. The use of a probability distribution compared to using a weight on the or each dose-distribution-derived function may also be advantageous because the probability distribution provides more information for the optimization process. More information for the optimization process may therefore lead to a more efficient and effective optimization process and therefore a more effective second treatment plan.

Step 404 comprises receiving or deriving a second probability distribution. The method may comprise deriving a plurality of probability distributions, i.e. second, third, fourth probability distributions and so on—one for each objective function to be used in the MCO problem. Like the first probability distribution, the second probability distribution may be considered to represent a degree of preference or a degree of achievability for a range of the values output from said dose-distribution-derived functions for an input dose distribution. Likewise, the second probability distribution may comprise a joint probability distribution or a plurality of marginal probability distributions as described above for the first probability distribution.

In one or more examples, the method comprises modifying said first probability distribution to form the second probability distribution. Different modifications may be made to form the third, fourth and any other probability distributions. It will also be appreciated that the (e.g. third) probability distribution may be formed by modifying any other probability distribution, (e.g. the first or second probability distribution).

The use of a first and at least a second probability distribution in an MCO process may also be advantageous because the use of different probability distributions, as will be described below, may provide an effective way of generating the different objective functions and the different treatment plans that are output from an MCO process. Further, given that the probability distributions represent a range of values along with a degree of preference or achievability for those values, the probability distributions can have different shapes to drive the optimization in a different way, such as to be more aggressive towards reaching a dose-measure value. This has been found to result in output treatment plans of high clinical quality as well as diversity, thereby providing the treatment planner with more options for treatment planning.

In the description that follows we describe various ways for obtaining the first and at least second probability distributions such that they are different and also different ways of modifying the first probability distribution to form the second probability distribution, as summarised by steps 403 and 404.

The step 403 may comprise receiving a current patient image (or other representation of the volume) representing said volume of the patient to be treated and information identifying at least one bodily structure in said current patient image. Such a patient image may be known as a contoured patient image and typically identifies the tumour, organs at risk and, optionally, other structures. This information may enable a fair comparison between the current patient image and the historic patient images in the process that follows.

The first probability distribution may be based on historic data of previously delivered treatment plans. This may be advantageous in that it provides a means of understanding what is likely to be achievable. Thus, the first probability distribution may be representative of the outcomes of the dose-measure values of the dose-distribution-derived functions of step 402, given the (e.g. contoured) current patient image and a plurality of previously delivered treatment plans with their respective (e.g. contoured) images. Accordingly, in one or more examples, the first probability distribution is determined from a database of previously delivered treatment plans, wherein the probability distribution is representative of the likelihood of a range of the values of the at least one dose-distribution-derived function being achieved based on the dose distributions achieved in previously delivered treatment plans. Thus, by assessing the dose-distribution-derived functions of step 402 using the dose distributions achieved in the historic treatment plans and their respective contoured) patient images, a likelihood that a dose-measure can be achieved for the current patient can be determined and represented by the first probability distribution.

It will be appreciated that the size and position of the tumour may differ in the historic treatment plans, as can the size and shape of the volume to be treated. Accordingly, the method may additionally include processing to account for those differences.

In general terms, parts of the volume treated in the historic treatment plans may be correlated to the parts of the volume in the current patient image, so that the historic dose distribution in the corresponding volumes can be used to derive the first probability distributions.

The method may include accessing a database 106 having a plurality of records that represent dose distributions of previously delivered treatment plans and respective patient images with information identifying at least one bodily structure in said images.

The method then comprises determining a measure of similarity between the current patient image (or other representation of the volume) and each of the patient images of said records, at least with respect to one or more of said at least one bodily structure. Thus, the method may rate, using a predetermined measure, similarities in the position and/or size and/or shape of the bodily structures. In one or more examples, known image similarity algorithms may be used.

The method, in one or more examples, may include evaluating one or more of the dose-distribution-derived functions received for the current patient in step 402 using the plurality of dose distributions of said records to obtain a dataset of values of the dose-distribution-derived function for each dose distribution.

The method can then include determining, from said dataset, said first probability distribution, corresponding to said evaluated one or more dose-distribution-derived functions, in a process comprising the use of a mapping function that gives a greater weighting to values of the dataset that correspond to a patient image having a greater measure of similarity with the current patient image and a lesser weighting to values of the dataset that correspond to a patient image having a greater measure of similarity with the current patient image. Thus, the mapping function may provide a relation between the determined measure of similarity and a degree to which the determined dose measures for the historic patient image and dose distribution contributes to the determination of the first probability distribution.

The mapping function can take various forms but should give greater weight to the data records in which the historic patient image and bodily structures thereof are similar to the current patient image and less weight to the data records in which the historic patient image and bodily structures thereof are dissimilar, according to the measure of similarity. The mapping function may be linear function or a higher order function or take other forms.

It will be appreciated that the method of determining a measure of similarity and then using a mapping function as described above may be implemented as a process derived from machine learning.

In one or more examples, this example method of deriving the probability distributions based on the measure of similarity between the current patient image and each of the patient images is applied for dose-distribution-derived functions that are configured to provide their respective values based on an input dose distribution represented as a dose-volume histogram. Thus, for such a dose-distribution-derived function, its output value only depends on the dose-volume histogram of the region of interest over which the function is defined. That is, its values for two dose distributions will coincide whenever the dose-volume histograms in the region of interest for said two dose distributions coincide.

In one or more examples, a different method of determining the first probability distribution may be used, such as for dose-distribution-derived functions that are single-voxel functions. Said single-voxel functions comprise dose-distribution-derived functions that are configured to provide an output equal to the dose delivered to a particular single voxel. In such an instance, the method may comprise using a spatial dose prediction model trained to predict the spatial dose distribution (the spatial distribution of the dose over the volume) of the current patient based on the patient image and information identifying at least one bodily structure in said historic patient image. Thus, a model derived from a machine learning process may be used rather that said measure of similarity. It will be appreciated that the dose prediction model could be used for dose-distribution-derived functions that are not single-voxel functions.

In one or more examples, the techniques used to determine the first probability distribution, depending on the types of dose-distribution-derived functions, may result in the first probability distribution being represented as the composition of several probability distributions. Thus, for example, the probability distribution over the dose-measure values of a set of dose-distribution-derived functions may be represented by the associated probability distributions of each of said dose-distribution-derived functions. It will be appreciated that a joint probability distribution may be derived from the constituent marginal dose-distribution-derived functions and such a process will be known to those skilled in the art including assumptions that may need to be made.

The first probability distribution may comprise a continuous function over a range of dose-measure values.

We now consider an example method of determining the first probability distribution, summarized above, in more detail.

Step 402 provides, in this example, a plurality of dose-distribution-derived functions $\psi_1$, $\psi_2$, ..., each being a function of the dose distribution d of the current patient, that is as represented in volume in the current patient image. The method requires us to predict their values $\psi_1(d)$, $\psi_2(d)$, ... on the current patient using the historic data records. The values $\psi_1(d)$, $\psi_2(d)$, ... are unknown and therefore they can be modelled as random variables. This prediction can be performed as a machine learning problem where the training data comprises pairs $\{(x^n, d^n)\}_n$ of historic patient images $x^n$ and historic dose distributions $d^n$, and where the goal is to obtain for the current patient with image x the prediction of $\psi_1(d)$, $\psi_2(d)$, ..., which amounts to estimating the conditional probability distribution $$p(\{\psi_j(d)\}_j | x, \{(x^n, d^n)\}_n).$$

where j designates each of the dose-distribution-derived functions and where p is used to denote probability density functions in general.

In one or more examples, the measure of similarity is represented by "accuracies" $a_1$, $a_2$, .... Thus, as summarized above, $a_n$, represents a notion of similarity between the current patient image x and the historic patient image $x^n$. An example algorithm for determining $a_n$ is outlined in McIntosh et al (2017), Fully automated treatment planning for head and neck radiotherapy using a voxel-based dose prediction and dose mimicking method, Physics in Medicine & Biology, 62(15), 5926-5944. It will be appreciated that other similarity algorithms may be used.

When the dose-distribution-derived functions $\psi_1$, $\psi_2$, ..., are configured to provide their respective values based on an input dose distribution for part or all of the volume represented as a dose-volume histogram (so-called DVH based dose-distribution-derived functions), it is possible to evaluate $\psi_1$, $\psi_2$, ... on the historical dose distributions of the data record. Thus, using the information that identifies the bodily structure(s) in the image, a corresponding region of interest in each of the historical patients can be found for each region of interest of the current patient. Then, the method can include inputting the corresponding dose-volume histogram to the dose-distribution-derived functions.

As mentioned above, the measures of similarities are used as basis for estimating the probability distribution by weighting the previously evaluated values by a mapping function. The mapping function may comprise a monotone transformation τ of the measures of similarity $a_n$—that is, the more similar a historical patient image $x^n$ is to the current image x, the closer the prediction of $\{\psi_j(d)\}_j$ will be to the corresponding evaluated values $\{\psi_j(d_n)\}_j$.

In one or more examples, the first probability distribution may take the form of a Gaussian mixture model. The determination of the first probability distribution as a Gaussian mixture model is summarized below.

As mentioned above the function τ comprises a monotonically increasing function (that is, such that $\tau(t) \leq \tau(t')$ whenever $t \leq t'$), e.g. $\tau(t) = t^2$.

If we let $y = (\psi_j(d))_j$ and $y^n = (\psi_j(d^n))$ for all n, we let $\theta = (\phi_c, \mu_c, \Sigma_c)_{c=1}^C$ (wherein $\phi_c$, $\mu_c$, $\Sigma_c$ comprise "class weights", "mean" and "covariances" respectively) be the parameters of a Gaussian mixture model with C classes (C may comprise a default value used by the method), which will comprise the parameters of the probability distribution of the DVH-based dose-distribution-derived functions—that is, $$p(y|\theta) = \sum_{c=1}^{C} \frac{\phi_c}{\sqrt{(2\pi)^k |\Sigma_c|}} \exp\left(-\frac{1}{2}(y-\mu_c)^T \Sigma_c^{-1}(y-\mu_c)\right)$$

where k is the dimension of y and $|\Sigma_c|$ is the determinant of $\Sigma_c$. $\phi_c$ is the "class weight", $\Sigma_c$ is the "covariance", $\mu_c$ is the "mean" and T denotes transposition. The likelihood function of the data $\{(x^n, y^n)\}_n$ is assumed to be of the form:

$$p(\{y^n\}_n | x, \{x^n\}_n, \theta) = \prod_n p(y^n | \theta)^{\tau(a_n)}$$

The prior distribution $p(\theta)$ of the parameters may be selected or predetermined. Examples of distributions include a Dirichlet distribution for the class weights $\{\phi_c\}_c$ and Gaussian-Inverse-Wishart distributions for each mean-covariance pair $\mu_c$, $\Sigma_c$, wherein exact definitions of these distributions will be known to those skilled in the art. The posterior distribution $$p(\theta | x, \{(x^n, y^n)_n\}) \propto p(\{y^n\}_n | x, \{x^n\}_n, \theta) p(\theta)$$

wherein ∝ denotes proportionality, may be computed or approximately computed using algorithms known to those skilled in the art. Examples of such algorithms include Expectation-Maximization (EM) and Variational Bayes. In particular, in the present example, a maximum a posteriori EM may be used.

Once the posterior distribution is obtained, the sought predictive distribution $p(y|x, \{(x'', y'')\}_n)$ is given by $$p(y|x,\{(x'',y'')\}_n) = \int p(y|\theta)p(\theta|x,\{(x'',y'')\}_n)d\theta$$

Computing (or approximately computing) this integral can be done in several ways, for example by a Dirac delta or Laplace approximation of the posterior, by variational methods or by Markov Chain Monte Carlo methods, said methods being familiar to those skilled in the art. The resultant first probability distribution will be a Gaussian mixture model for some cases or a mixture of multivariate Student's t-distributions for other cases.

Determination of the first probability distribution for dose-distribution-derived functions that comprise single-voxel functions (that is, $\psi_j(d)=d_i$ for some voxel index i), one can instead use the measures of similarities an as basis for weighting together atlas regression forest models. The result of this is predictions in the form of marginal probability distributions $p(d_i|x, \{(x'', d'')\}_n)$ for each voxel i, from which one can obtain the joint probability distribution of all dose-distribution-derived functions by additional assumptions. In particular, in one or more examples, it may be assumed there is independence between the dose-measure values of dose-distribution-derived functions and a joint probability distribution can be derived from the marginal distributions and the independence assumption. This technique will be known to those skilled in the art.

The above more detailed description of the prediction of the values of the dose-distribution-derived functions is one example, and it will be appreciated that other dose prediction and/or DVH prediction algorithms may be used. Said other algorithms may use a measure of similarity and a mapping function in some form.

However, to summarise, in one or more examples, if the dose-distribution-derived function is configured to provide its respective value based on a predefined region of the volume and the input dose distribution is represented as a dose-volume histogram for said predefined region of the volume, the method comprises applying a weighting to said evaluated (on the historic dose distribution) dose-distribution-derived function(s) using the mapping function, wherein said mapping function may comprise a monotone transformation of the measure of similarity.

In one or more examples, if the dose-distribution-derived function comprises a single-voxel function, the method comprises using a spatial dose prediction model trained on data comprising historically delivered treatment plans to predict the spatial dose distribution of the current patient based on the patient image and information identifying at least one bodily structure in said image. The dose prediction model may comprise a model determined by machine learning to provide, for each voxel of the current image, information indicative of the predicted dose of said voxel of said current image. In one or more examples, said information may comprise a probability distribution representing the achievability or desirability of a range of dose values.

Thus, in general, there are several different ways of deriving the first probability distribution from the data records of the database 106 related to historically delivered treatment plans. It will also be appreciated that the first probability distribution may be a combination of marginal probability distributions that are formed using the above techniques along with user-drawn, or otherwise specified, probability distributions provided by user input.

Thus, a subset of a plurality of the dose-distribution-derived functions may have an associated probability distribution determined with reference to the data records of database 106, as described above, and the remaining dose-distribution-derived functions may be associated with a probability distribution input by the user. The first probability distribution may be represented by a combination of the marginal probability distributions determined in these different ways.

The step 404 may be provided by modification of the first probability distribution that was determined using the data records from database 106 (or using a different method of deriving the first probability distribution) to form the second probability distribution.

In one or more examples, the first probability distribution may be represented by a set of marginal probability distributions and the modification may apply to one, some or all of the marginal probability distributions.

The second probability distribution (and any component marginal distributions) may therefore comprise a modified version of the first probability distribution (and any corresponding component marginal distributions), wherein the modification applied to the first probability distribution to form the second probability distribution may comprise one or more of:

a change of a mean value of the first probability distribution;

a change in a standard deviation of the first probability distribution;

a change derived from exponential tilting of the first probability distribution; and a change of a skewness of the first probability distribution.

The degree of the change may be specified by user input. Alternatively, the degree of the change may be a predetermined amount. For example, the change applied to the mean of the probability distribution may be a predetermined number of standard deviations. The shape of the first probability distribution may be narrowed or widened by changing the standard deviation of the probability distribution, such as by a predetermined percentage change. Tilting and skewness may also be changed by predetermined amounts. Accordingly, the method may include determining one or more of the mean, standard deviation, skewness or tilt of the first probability distribution and may determine a function to effect the change. The second probability distribution may then comprise the first probability distribution having the determined "change" function applied thereto.

In one or more examples, the first probability distribution is modified prior to being used in the MCO problem in step 405. For example the first probability distribution may be modified by the method including the step of providing for one or more of a change of a mean value of the first probability distribution; a change in a standard deviation of the first probability distribution; a change derived from exponential tilting of the first probability distribution; and a change of a skewness of the first probability distribution. Therefore, it will be appreciated that the second probability distribution is modified in a different way to any modification that may be applied to the first probability distribution.

The computer system 101 may be configured to provide for user input to define the modification to the first probability distribution to form the second probability distribution. The modification to make may be determined in different ways. For example, said modification may be determined based on user input defining said modification. Thus, the user may specify the change and, optionally, the degree of the change. Alternatively, the system 101 may provide for selection of one of a plurality of default modifications based on user selection.

In one or more examples, the method may include providing feedback to an output device 105 for a user so that the effect of the modification can be appreciated. In one or more examples, said feedback may be indicative of one or more of:
(i) the different shapes of the first probability distribution and the second probability distribution due to said modification, such as by showing the probability distributions diagrammatically;
(ii) the difference between characteristics of the first and second probability distributions due to said modification, such as in terms of numerical differences in one or more of the mean, standard deviation, exponential tilting or skewness;
(iii) an indication of how the dose-distribution for the volume will change due to said modification, such as by way of a graphical overlay on the image of the volume; and
(iv) the output treatment plan determined as a result of said modification.

The system 101 and method may therefore proceed on the basis of the user input that defines the modification, or user selection of one of the plurality of default modifications. In other examples, the modification is not shown to the user and instead may comprise a default modification.

In one or more examples, said default modification may be defined as a change in the mean or other characteristic by different numbers of standard deviations (e.g. one or two standard deviations) or by different predetermined percentages.

In the examples herein, the intention of the modification may be to transform the originally estimated probability distribution to be more focused/aggressive/optimistic on one, several or all of the dose-distribution-derived functions, thereby leading to the produced output treatment plans (in step 406 described below) reflecting different focuses. In general, the dose-measure value of each dose-distribution-derived function included in the objective function is to be either minimized or maximized ideally. For the former case, the probability distribution may be made more aggressive by shifting the mean down, for example. A lower standard deviation may also correspond to being more aggressive.

In the above examples, generating the second probability distribution by the modification of the first probability distribution is provided by making changes to its statistical parameters. However, in other examples, the second probability distribution may be generated in a different way. For example, in one or more examples, the second probability distribution is also generated using a database 106 of records in a similar manner to the first probability distribution. The database may be a different database containing different records to that used for the first probability distribution. The different database may be a database of dose distributions that were achieved from treatment plans that may have been categorised as being more aggressive (or other categorization) by a clinician. Alternatively, it may be the same database, but a different subset of records may be used for generating the second probability distribution compared to the first probability distribution. In one or more examples, the records of the database may be categorised into a plurality of record sets and the first probability distribution may be generated from the one record set and the second probability distribution may be generated from a different record set. The difference between the record sets may be defined by a clinician or an automated process.

In a further example, the second probability distribution is also generated using a database of records 106 in a similar manner to the first probability distribution. However, in one or more examples, a different mapping function is used to provide the different first and second probability distributions. It will be appreciated that the use of a different mapping function has the same effect as modifying the first probability distribution to generate the second probability distribution, because both probability distributions are based on the same underlying data, but a modification has been introduced between them. In this example, the modification is introduced into the mapping function rather than as a post-processing change in the statistical properties of the first probability distribution.

FIG. 2 shows an example first and second probability distributions. The x-axis 201 shows the range of values output by the dose-distribution-derived function or functions and the y-axis shows the likelihood of the values being achieved based on the data records. The first probability distribution 203 is plotted. The second probability distribution 204 is generated by creating a modified version of the first probability distribution. In this schematically represented example, the mean and the skewness has been modified to create the second probability distribution 204.

Example FIG. 3 shows an annotated dose-volume histogram 300 representing two dose distributions 301, 302 for different regions of the volume (the tumour and an organ at risk). The dose-distribution-derived functions are defined for the two different regions of the volume, indicated by arrows 303 and 304. For each dose-distribution-derived function 301, 302 a probability distribution 305 and 306 is also defined (which collectively form the first probability distribution).

In one or more examples, the probability distribution 305, 305 over the respective dose-distribution-derived function 303, 304, effectively assigns a corresponding likelihood of a dose-measure value (output from the dose-distribution-derived function given an input dose distribution) being achieved/acceptable/satisfactory in a treatment plan. The one probability distribution 306 is wide and symmetric, which may indicate that the clinician is accepting of a wider range of dose-measure values around the target dose-measure value. The other probability distribution 305 is narrower and skewed, which may indicate that the clinician is less accepting of dose-measure values on one side of a target dose-measure value than the other side. The marginal probability distributions that form the second probability distribution may be modified to narrow the distribution 306 to be more selective of a particular dose measure and may change the mean of the distribution 305 to be more aggressive to achieve a higher dose to the tumour.

The historical data may be indicative of how precisely dose-measure target may be met and the shape/defining characteristics of the probability distribution may reflect this.

As mentioned above, the first probability distribution and the second probability distributions are joint probability distributions over the one or more dose-distribution-derived functions. In one or more examples, the first probability distribution and the second probability distributions are all represented by a set of marginal probability distributions for each of the dose-distribution-derived functions. In more detail, once the set of dose-distribution-derived functions is defined, a probability distribution of a multidimensional real random variable, with dimensionality equal to the number, n, of dose-distribution-derived functions, may also be specified. Such a probability distribution may be derived from the marginal probability distribution of each dose-distribution-derived function, provided assumptions are made regarding independence or information indicative of the correlations between the dose-distribution-derived functions is available, as will be appreciated by those skilled in the art. A probability distribution of a n-dimensional random variable $X=(X_1, X_2, \ldots, X_n)$ is uniquely determined by its cumulative distribution function $F_X$ taking n real numbers as input and giving a number in the interval [0,1] as output, in such a way that $F_X(x_1, x_2, \ldots, x_n) \leq F_X(y_1, y_2, y_n)$ for all pairs $(x_1, x_2, \ldots, x_n)$, $(y_1, y_2, \ldots, y_n)$ of realizations of X and Y, respectively, such that $x_i \leq y_i$ for all $i=1, 2, \ldots, n$;

$$\lim_{h \to 0^+} F_X(x_1, \ldots, x_{i-1}, x_i + h, x_{i+1}, \ldots, x_n) = F_X(x_1, \ldots, x_{i-1}, x_i, x_{i+1}, \ldots, x_n)$$

for all $i=1, 2, \ldots, n$;

$$\lim_{x_1, x_2, \ldots, x_n \to \infty} F_X(x_1, x_2, \ldots, x_n) = 1; \text{ and}$$

$$\lim_{x_i \to -\infty} F_X(x_1, x_2, \ldots, x_n) = 0 \text{ for all } i = 1, 2, \ldots, n.$$

Thus, in one or more examples, the probability distribution for the set of dose-distribution-derived functions is represented as a cumulative distribution function. However, a probability distribution may be specified in different ways and the cumulative distribution function is only one way.

For each component $X_i$, the marginal cumulative distribution function $F_{X_i}$ is given by the integral:

$$F_{X_i}(x_i) = \int F_X(x_1, x_2, \ldots, x_n) dx_{j \neq i},$$

where $x_{j \neq i} = (x_1, \ldots, x_{i-1}, x_{i+1}, \ldots, x_n)$.

Thus, in one or more examples, the probability distribution is represented by the marginal cumulative distribution functions $F_{X_i}$, $i=1, 2, \ldots, n$. It will be appreciated that in one or more examples, it is sufficient to specify the marginal cumulative distribution function associated with each of the constituent dose-distribution-derived functions for the corresponding optimization problem to be fully defined. In one or more examples, one can recover the cumulative distribution function $F_X$ over X from the marginal cumulative distribution functions $F_{X_i}$ of all $X_i$ by additional assumptions on the distributional characteristics of X. Thus, in one or more examples, one assumes that X follows a mixture of multivariate normal distributions and that the correlation between each pair $X_i$, $X_j$ in each mixture class is given (e.g. by user input or as predetermined values); from this, the cumulative distribution function $F_X$ can be determined by a process which will be known to those skilled in the art.

Example step 405 comprises defining a multi-criteria optimization problem comprising at least two objective functions comprising:

a first objective function of the at least one dose-distribution-derived function, the first probability distribution (which may or may not be a modified version of the probability distribution derived from the historic data) and a loss function; and a second objective function of the at least one dose-distribution-derived function, the second probability distribution and the loss function.

The number of objective functions may therefore be dependent on the number of probability distributions. Thus, the method may include the determination of a third probability distribution by a further modification of the first probability distribution or second probability distribution. Accordingly, the multi-criteria optimization problem may then include a third objective function of the at least one dose-distribution-derived function, the third probability distribution and the loss function. Further objective functions may be defined in the same way.

In this example, the same loss function is used in each objective function, but in other examples different loss functions may be used. The loss function may be selected from one or more of a logarithmic loss function and a cross-entropy loss function among others.

The loss function and the respective probability distribution may act as the rating scale function described earlier.

Step 405 may include determining each objective function upon which to perform the multi-criteria optimization process, i.e. solve or partially solve the optimization problem, each objective function being of at least one variable comprising a parameter that defines the respective output treatment plan. The modification of the at least one variable is configured to affect at least one of the dose-measure values output by the dose-distribution-derived functions, and wherein the determination of each of the objective functions is based on the dose-distribution-derived functions and their respective the probability distribution.

Step 405 may include converting the one or more dose-distribution-derived functions into objective functions, which may define the optimization problem, by applying a respective loss function to each dose-distribution-derived function and its associated probability distribution.

An example of how to derive the first and second objective functions from the dose-distribution-derived functions and the first and second probability distributions respectively to form the MCO problem is as follows:

Step 402 provides a set (e.g. one or more) of n dose-distribution-derived functions $\psi_1, \psi_2, \ldots, \psi_n$ of the dose distribution d and step 403, 404 provides an associated first or second probability distribution e.g. for the set.

To determine the first objective function $\psi_{first}$ (determination of the second objective function $\psi_{second}$ is the same except the second probability distribution is used):

Let $\eta$ denote the plan parameters we use to represent the output treatment plan. The plan parameters may, for example, comprise operating parameters of the device 107 and from which a dose distribution can be derived, but in principle the plan parameters could be any parameters uniquely determining the dose distribution. It will be appreciated that the corresponding dose distribution $d=d(\eta)$ is completely determined by the plan parameters. The function $d(\eta)$ that translates the plan parameters to a dose distribution may be predetermined and may be known to those skilled in the art.

The optimization problem defined in step 405 to be solved in step 406 is:

Minimize $\psi_{first}(\eta)$ subject to $\eta$ satisfying any constraints that may be user provided or technical constraints of the radiation therapy delivery device 107.

In one or more examples, the method may use the weighted-sum form $$\psi_{first}(\eta) = \sum_{i=1}^{M} w_i \psi_i(\eta).$$

It will be appreciated that the M objective function parts that form the first objective function may be equal to or less than the number n of dose-distribution-derived functions. Thus, in one or more examples, two or more of a plurality of dose-distribution-derived functions may be combined into one objective function.

The setup may comprise the following steps:
1. Decide on the number of function parts M and the weights $w_i$. The system 101 may receive user input to specify these values or may have default values. For example, M may equal two and the dose-distribution-derived functions may be split into two groups: single-voxel functions and non-single voxel functions. The functions of each of the two groups may therefore be combined into two objective function parts that form the first objective function.
2. For each i=1, 2, . . . M:
    a. Decide on the index set $S_i$, which is a subset of all indices $\{1, 2, \ldots, n\}$. The system 101 may receive user input to specify $S_i$ values or a default value may be used.
    b. Decide on a parametrization of the first probability distribution over the values of the dose-distribution-derived functions $\{\psi_j\}_{j \in S_i}$ in the index set, e.g. the cumulative distribution function $F_X$ or the probability density function $f_X$, where $X=(X_1, X_2, \ldots, X^n)$ is a vector-valued random variable. This can be decided by either user input or a predetermined algorithm. One example way is to use the probability density function for dose-distribution-defined functions of single-voxel type and a cumulative distribution function otherwise.
    c. Decide on a loss function L, taking as input the output of the parametrization in 2b and giving as output a number representing the loss contribution upon observing said output of the parametrization. For example, L could be the logarithmic loss $L(t)=-\log t$ or the cross-entropy loss $L(t)=-a \log t-(1-a)\log(1-t)$, where $a \in \{0,1\}$. Again, the choice of loss function may be received by user input or a predetermined loss function may be selected. In one or more examples, the choice of loss function may be based on the type of dose-distribution-defined function e.g. single voxel type or non-single voxel type.
    d. Depending on whether we used $F_X$ or $f_X$ (suppose the former), obtain $\psi_i$ as $$\psi_i(\eta)=L(F_X(\{\psi_j(d(\eta))\}_{j \in S_i}))$$

As an example, suppose that we want to group the dose-distribution-derived functions into lower/upper peak-seeking (get as low/high as possible), and tail-seeking (get as close to the mode as possible). We would then use the cumulative distribution function and the cross-entropy loss with a 0/1 for the former cases, and a probability density function and a log-loss on the latter case. Here, the index set represents the relevant indices of the functions.

Thus, to summarize, in one or more examples, the first objective function is determined using one or more of the dose-distribution-derived functions and the first probability distribution and a loss function. Thus, the first objective function $\psi_{first}$ incorporates the at least one dose-distribution-derived functions and the first probability distribution and is defined in terms of the plan parameters of the output treatment plan. As described herein, the formulation of the optimization problem in this way is advantageous in terms of flexibility for selecting dose measures for guiding the optimization process.

It will be appreciated that the determination of the second objective function $\psi_{second}$ is similar, with step 2b relating to the second probability distribution. The selection of any grouping of the dose-distribution-derived functions may be the same, but in principle could be different. The plan parameters 11 are the same.

As a more specific example, the method may be configured to determine the first objective function comprising at least one objective function part based on a respective at least one dose-distribution-defined function by:
(i) receiving the set of dose-distribution-derived functions, partitioned into an index set $S_1$ of all constituent single-voxel functions and an index set $S_2$ of all constituent functions which are not single-voxel functions;
(ii) for each function in $S_1$ and $S_2$, receive the associated probability distribution represented as marginal cumulative distribution function;
(iii) assume independence between the dose-measure values of all functions in $S_1$ and $S_2$ and obtain two cumulative distribution functions, one for those in $S_1$ and one for those in $S_2$ (how to derive of a cumulative distributions from the marginal distributions and the independence assumption is known to those skilled in the art);
(iv) for $S_2$, apply a cross-entropy loss function on the corresponding cumulative distribution function, which will define one objective function $\psi_2$;
(v) for $S_1$, differentiate to obtain from the cumulative distribution function from the corresponding probability density function and apply a log-loss function, which will define another objective $\psi_1$;
(vi) use equal weights $w_1=w_2=1$ to obtain the total objective function as $\psi_{tot}=\psi_1+\psi_2$.

In one or more examples, the present method is advantageous because it provides for greater flexibility in defining the MCO optimization problem. The use of the two different probability distributions (first and second and optionally third, fourth and so on) as the differentiator between the objective functions has been found to provide a convenient and effective way of defining the MCO problem and on average may yield a greater number of viable output treatment plans while still covering a sufficiently diverse range of possibilities.

Step 406 comprises solving (or partially solving) the MCO optimization problem determined in step 405. Thus, the system 101 may be configured to perform a multi-criteria optimization process based on said at least two objective functions to generate at least two output treatment plans. Step 406 may include finding variables (parameters of the output treatment plan) that minimize the first objective function subject to satisfying the constraints. Step 406 may include finding variables (parameters of the output treatment plan) that minimize the second objective function subject to satisfying the constraints, and so on for any other objective functions. It will however be appreciated that the solving of the MCO problem may include additional processes, which will be familiar to those skilled in the art.

Step 406 may comprise using, for example, the weighted-sum method or the epsilon-constraint method to obtain a desired number of Pareto optimal output treatment plans. It will be appreciated that a Pareto optimal plan is a treatment plan determined such that no objective function (first or second or other) can be improved without a deterioration in at least one of the others.

The output treatment plans may be used as input to a navigation or interpolation process.

The output treatment plans described herein are indicative of a dose distribution over said volume. Thus, a dose distribution over the volume can be calculated from the parameters of the output treatment plan or treatment plan parameters determined during the optimization process. In one or more examples, the parameters of the output treatment plan are "complete" in that they uniquely determine the corresponding dose distribution. The output treatment plans may be defined in a variety of ways. In one or more examples, the output treatment plan has parameters that define the operating parameters of the radiation therapy delivery device 107 and a dose distribution over said volume is calculated therefrom. In one or more other examples, the treatment plan has parameters that define the dose distribution. In one or more other examples, the treatment plan has parameters that define irradiation intensity integrated over time from each direction in space, comprising a so-called fluence map, and the dose distribution over said volume is determined therefrom. The algorithms used to derive the resulting dose distribution from the parameters of a treatment plan will be known to those skilled in the art.

Compared to existing approaches in automatic treatment planning using prior knowledge, the proposed method is able to capture more accurately preferences with respect to clinical goals represented in the dose-distribution-derived functions. In comparison to conventional MCO, the Pareto optimal output treatment plans generated are such that they cover more exactly a clinically relevant dose region. The use of a complete probability distribution over the dose-distribution-derived functions removes the need for e.g. generating sample plans in order to be able to produce Pareto optimal plans. The first and second objective functions are able to leverage probabilistic information such as prediction uncertainties, which is typically discarded in prior art, reducing the need for various ad hoc constructions used to make the optimization work out well. The method of using one or more modifications of the first probability distribution to construct the MCO problem from an "ordinary" optimization problem may be considered a major contribution. Also, formulating the MCO problem in this way avoids the use of non-linear constraints, which may make the MCO problem more computationally efficient to solve.

With the MCO problem yielding a plurality of output treatment plans, the method may include determining a final treatment plan based on the at least two output treatment plans. The determination of the final treatment plan may be based on user input, such as a user selection of one over the others. In other examples, the determination may be automated. For example, in one or more examples, the method may include automated scoring of the at least two output treatment plans based on predefined criteria and the determination of the final treatment plan may be based on the output treatment plan that received the highest score.

In other examples, the method may provide for determination of a final treatment plan by interpolation between the two or more output treatment plans. Thus, based on user input, the system 101 may be configured to interpolate between the output treatment plans to define an interpolated treatment plan as the final treatment plan. In particular, the output treatment plans are defined in terms of one or more plan parameters η and the method comprises, based on user input, interpolating one or more of said plan parameters η between the values specified in said output treatment plans to define the interpolated treatment plan as the final treatment plan. A graphical user interface having user operated sliders that control the degree of interpolation may be provided.

Step 407 comprises an optional step of configuring or programming the radiation therapy delivery device 107 using one of the output treatment plans or the final treatment plan for delivery of radiation therapy in accordance with the output/final treatment plan.

The method described herein may be advantageous in one or more examples in that it provides the ability to choose arbitrary dose-distribution-defined functions to generate the total objective function. For example, one can directly put in evaluation criteria such as clinical goals. This allows for a natural way of articulating which aspects of the resulting dose distributions are important and which are not. Further, the probability distributions, in one or more examples, are able to capture nuances of the preferences of the user or the achievability of particular dose measures (based on the historic data records) that are more complex than only using quadratic penalties. In one or more examples, the method may also handle trade-offs between different goals more effectively due to the use of the first and second probability distributions. By using first and second probability distributions to define the objective functions of the MCO problem, different nuances can be captured and used in the MCO process.

It will be appreciated that in one or more examples, the method includes the step of receiving one or more constraints, wherein the output treatment plan is defined in terms of a set of first plan parameters and the one or more constraints define values that the parameters of the output treatment plan can and/or cannot take in said optimization. For example, the output treatment plan may be defined in terms of parameters related to the radiation therapy delivery device 107 and the constraints may therefore relate to technical limitations of the radiation therapy delivery device, such as terms of maximum gantry rotation speeds or maximum power output. In other examples, the constraints may represent limits to the dose-distribution for the volume or sub-volumes thereof.

Figure 5:
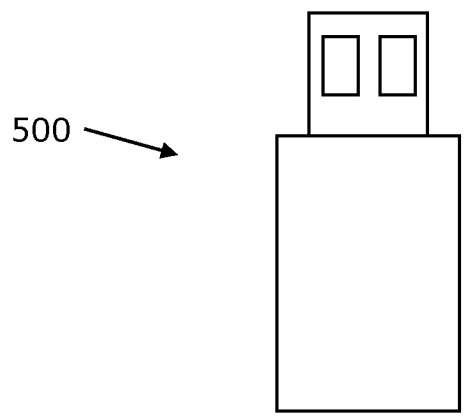
FIG. 5 shows an example computer readable medium.

Example FIG. 5 shows a computer readable medium 500, as an example of a computer program product. The computer readable medium may comprise a non-transitory computer readable medium. The computer readable medium 500 contains a computer program comprising computer program code that, when executed by an apparatus, such as computer system 201 having a processor 202 and memory 203, is configured to perform the method described herein.

The instructions and/or flowchart steps in the above figures can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

In some example embodiments the method steps described above are implemented as functional and software instructions embodied as a set of executable instructions which are effected on a computer or machine which is programmed with and controlled by said executable instructions. Such instructions are loaded for execution on a processor (such as one or more CPUs). The term processor includes microprocessors, microcontrollers, processor modules or subsystems (including one or more microprocessors or microcontrollers), or other control or computing devices. A processor can refer to a single component or to plural components.

In other examples, the methods illustrated herein and data and instructions associated therewith are stored in respective storage devices, which are implemented as one or more non-transient machine or computer-readable or computer-usable storage media or mediums. Such computer-readable or computer usable storage medium or media is (are) considered to be part of an article (or article of manufacture). An article or article of manufacture can refer to any manufactured single component or multiple components. The non-transient machine or computer usable media or mediums as defined herein excludes signals, but such media or mediums may be capable of receiving and processing information from signals and/or other transient mediums.

Example embodiments of the material discussed in this specification can be implemented in whole or in part through network, computer, or data based devices and/or services. These may include cloud, internet, intranet, mobile, desktop, processor, look-up table, microcontroller, consumer equipment, infrastructure, or other enabling devices and services. As may be used herein and in the claims, the following non-exclusive definitions are provided.

In one example, one or more instructions or steps discussed herein are automated. The terms automated or automatically (and like variations thereof) mean controlled operation of an apparatus, system, and/or process using computers and/or mechanical/electrical devices without the necessity of human intervention, observation, effort and/or decision unless otherwise indicated as requiring user input.

In this specification, example embodiments have been presented in terms of a selected set of details. However, a person of ordinary skill in the art would understand that many other example embodiments may be practiced which include a different selected set of these details. It is intended that the following claims cover all possible example embodiments.

The invention claimed is:

1. A computer-implemented method for generating a radiation therapy treatment plan for a volume of a patient, the method being performed in a treatment planning system and comprising the steps of:
   receiving an image of the volume;
   receiving at least one dose-distribution-derived function, the at least one dose-distribution-derived function configured to provide a value as an output based on, as an input, at least part of a dose distribution defined relative to the image;
   receiving a first probability distribution and at least a second, different, probability distribution, the first and at least second probability distributions indicating an achievability or desirability of a range of values output from the at least one dose-distribution-derived function;
   defining a multi-criteria optimization problem comprising at least two objective functions comprising:
      a first objective function based on the at least one dose-distribution-derived function, the first probability distribution and a loss function; and
      a second objective function based on the at least one dose-distribution-derived function, the at least, a second probability distribution and the loss function; and
   performing a multi-criteria optimization process based on the at least two objective functions to generate at least two output treatment plans, wherein each treatment plan among the at least two output treatment plans is configured to deliver a radiation dose to the patient when the treatment plan is executed on a treatment machine.

2. The computer-implemented method of claim 1, wherein the method comprises modifying the first probability distribution to form the at least a second probability distribution.

3. The computer-implemented method of claim 2, wherein the modification of the first probability distribution to form the at least a second probability distribution comprises one or more of:
   a change of a mean value of the first probability distribution;
   a change in a standard deviation of the first probability distribution;
   a change derived from exponential tilting of the first probability distribution; and
   a change of a skewness of the first probability distribution.

4. The computer-implemented method of claim 1, wherein the method includes modifying the first probability distribution to form a modified version thereof prior to defining the multi-criteria optimization problem and wherein the at least two objective functions comprise:
   the first objective function based on the at least one dose-distribution-derived function, the modified version of the first probability distribution and the loss function; and
   the second objective function based on the at least one dose-distribution-derived function, the at least a second probability distribution and the loss function.

5. The computer-implemented method of claim 1, wherein the first probability distribution is determined from a database of previously delivered treatment plans, and indicates a likelihood of achieving a range of the values for the at least one dose-distribution-derived function, wherein the likelihood is determined based on dose distributions achieved in previously delivered treatment plans.

6. The computer-implemented method of claim 5, wherein the step of receiving the first probability distribution comprises:
   receiving a current patient image, x, comprising the image of the volume of the patient to be treated and information identifying at least one bodily structure in the image; and
   based on the at least one dose-distribution-derived functions, $\{\psi_{jj}\}_{jj}$, each comprising a function of a dose distribution, d, over the current patient image, estimating the conditional probability distribution:

$$p(\{\psi_j(d)\}_j | x, \{(x'', d'')\}_n$$

using a machine learning process trained using training data comprising pairs $\{(x'', d'')\}_n$ of historic patient images $x''$ with information identifying the at least one bodily structure in the image and corresponding historic dose distributions $d''$ achieved in previously delivered treatment plans, the conditional probability distribution thereby being indicative of a likelihood of a range of outputs from the dose-distribution-derived functions for the dose distribution, d, for the current patient based on the dose distributions achieved for historic patients.

7. The computer-implemented method of claim 5, wherein the first probability distribution comprises a Gaussian mixture model wherein parameters of the Gaussian mixture model are determined based on the at least one dose-distribution-derived function and dose distributions derived from the database of previously delivered treatment plans.

8. The computer-implemented method of claim 1, wherein the method comprises:
receiving a current patient image comprising the image of the volume of the patient to be treated and information identifying at least one bodily structure in the image;
accessing a database having a plurality of records of dose distributions for previously delivered treatment plans and respective patient images with information identifying the at least one bodily structure in the images;
determining a measure of similarity between the current patient image and each of the patient images of the records, at least with respect to the at least one bodily structure;
evaluating one or more of the at least one dose-distribution-derived functions received for the current patient image using the plurality of dose distributions of the records to obtain a dataset of values of the dose-distribution-derived function for each dose distribution in the plurality of dose distributions;
determining, from the dataset, the first probability distribution, corresponding to the evaluated one or more dose-distribution-derived functions, using a mapping function that gives a greater weighting to values of the dataset that correspond to a patient image having a greater measure of similarity with the current patient image and a lesser weighting to values of the dataset that correspond to a patient image having a lesser measure of similarity with the current patient image.

9. The computer-implemented method of claim 8, wherein
when the dose-distribution-derived function is configured to provide a respective value based on a predefined region of the volume and an input dose distribution is a dose-volume histogram for the predefined region of the volume, the method comprises applying a weighting to the evaluated one or more dose-distribution-derived functions using the mapping function, wherein the mapping function comprises a monotone transformation of the measure of similarity; and
when the dose-distribution-derived function comprises a single-voxel function, wherein the patient image is formed of a plurality of voxels and the dose-distribution-derived function is configured to provide an output equal to a dose delivered to a particular single voxel, the method comprises using a dose prediction model trained to predict a dose distribution of the current patient based on the patient image and information identifying the at least one bodily structure in the image.

10. The computer-implemented method of claim 1, wherein the method comprises, based on user input, interpolating between the at least two output treatment plans to define an interpolated treatment plan as a final treatment plan of the method.

11. The computer-implemented method of claim 1, wherein one or more of the at least one dose-distribution-derived functions is defined such that an output value from the one or more of the at least one dose-distribution-derived functions cannot be determined solely by a dose-volume-histogram of the at least part of the dose distribution.

12. The computer-implemented method of claim 1, wherein the step of receiving the at least one dose-distribution-derived function comprises one or more of:
receiving a user input to define one or more of the dose-distribution-derived functions; and
selecting one or more dose-distribution-derived functions from a set of candidate dose-distribution-derived functions, the candidate dose-distribution-derived functions comprising predetermined functions selected based on a part of the body of the patient in which the volume is defined.

13. The computer-implemented method of claim 1, wherein the at least one dose-distribution-derived function comprises, for the whole volume or part thereof, one or more of dose-at-volume, volume-at-dose, average dose, homogeneity comprising a measure of the dose homogeneity in the whole or part volume, conformity index, and a penalty function, including minimum-dose, maximum-dose or a dose-volume histogram function.

14. An apparatus for generating a radiation therapy treatment plan, the apparatus comprising a processor and a memory and computer program code stored in the memory, the computer program code configured to, when executed by the processor, cause the apparatus to perform the method of claim 1.

15. A computer program product comprising a non-transitory, computer readable storage medium containing computer program code that, when executed by a processor, is configured to perform the method of claim 1.

* * * * *